(12) United States Patent
Cruise et al.

(10) Patent No.: US 11,135,167 B2
(45) Date of Patent: *Oct. 5, 2021

(54) POLYMER PARTICLES

(71) Applicant: Terumo Corporation, Tokyo (JP)

(72) Inventors: Gregory M. Cruise, Rancho Santa Margarita, CA (US); Gloria Hincapie, Aliso Viejo, CA (US); Clayton Harris, Aliso Viejo, CA (US)

(73) Assignee: Terumo Corporation, Tokyo (JP)

( * ) Notice: Subject to any disclaimer, the term of this patent is extended or adjusted under 35 U.S.C. 154(b) by 87 days.

This patent is subject to a terminal disclaimer.

(21) Appl. No.: 16/516,931

(22) Filed: Jul. 19, 2019

(65) Prior Publication Data

US 2019/0338059 A1 Nov. 7, 2019

Related U.S. Application Data

(63) Continuation of application No. 16/175,609, filed on Oct. 30, 2018, now Pat. No. 10,400,051, which is a (Continued)

(51) Int. Cl.
*A61K 9/16* (2006.01)
*C08L 33/14* (2006.01)
(Continued)

(52) U.S. Cl.
CPC .......... *A61K 9/1635* (2013.01); *A61K 9/0029* (2013.01); *A61L 24/001* (2013.01); *A61L 24/06* (2013.01); *A61L 31/048* (2013.01); *C08F 220/38* (2013.01); *C08F 220/56* (2013.01); *A61K 9/19* (2013.01); *A61L 2430/36* (2013.01); *C08F 220/382* (2020.02); *C08F 222/1006* (2013.01); *C08F 222/385* (2013.01); *C08F 222/408* (2020.02); *C08L 33/02* (2013.01);
(Continued)

(58) Field of Classification Search
None
See application file for complete search history.

(56) References Cited

U.S. PATENT DOCUMENTS 4,070,348 A 1/1978 Kraemer et al.
4,157,323 A 6/1979 Yen et al.
(Continued)

FOREIGN PATENT DOCUMENTS

CN 103709323 A 4/2014
EP 0240424 B1 5/1991
(Continued)

OTHER PUBLICATIONS

Blinova et al., Poly(ethylene glycol) containing functionalized polymer membranes for carbon dioxide separation. Preprints—American Chemical Society, Division of Energy & Fuels, 59(1):433-434 (2014).
(Continued)

*Primary Examiner* — Richard A Huhn
(74) *Attorney, Agent, or Firm* — K&L Gates LLP; Brian J. Novak; Benjamin D. Heuberger

(57) ABSTRACT

Biodegradable, cross-linked polymer particle embolics and methods of making the same are described. The particle embolics can be used as embolization agents.

20 Claims, 2 Drawing Sheets

Related U.S. Application Data continuation of application No. 15/910,976, filed on Mar. 2, 2018, now Pat. No. 10,144,793, which is a continuation of application No. 15/630,048, filed on Jun. 22, 2017, now Pat. No. 9,938,367, which is a continuation of application No. 15/369,213, filed on Dec. 5, 2016, now Pat. No. 9,803,043, which is a continuation of application No. 14/491,776, filed on Sep. 19, 2014, now Pat. No. 9,546,236.

(60) Provisional application No. 61/880,036, filed on Sep. 19, 2013.

(51) Int. Cl.
| | |
|---|---|
| *C08F 220/56* | (2006.01) |
| *A61L 24/00* | (2006.01) |
| *A61L 24/06* | (2006.01) |
| *C08F 220/38* | (2006.01) |
| *A61L 31/04* | (2006.01) |
| *A61K 9/00* | (2006.01) |
| *C08F 222/10* | (2006.01) |
| *C08F 222/38* | (2006.01) |
| *C08F 222/40* | (2006.01) |
| *A61K 9/19* | (2006.01) |
| *C08L 33/02* | (2006.01) |
| *C08L 33/26* | (2006.01) |

(52) U.S. Cl.
CPC ............. *C08L 33/14* (2013.01); *C08L 33/26* (2013.01); *C08L 2203/02* (2013.01); *C08L 2312/00* (2013.01); *Y10T 428/2982* (2015.01)

(56) References Cited

U.S. PATENT DOCUMENTS

| | | | |
|---|---|---|---|
| 4,925,677 A | 5/1990 | Feijen | |
| 5,417,982 A | 5/1995 | Modi | |
| 5,545,423 A | 8/1996 | Soon-Shiong et al. | |
| 5,635,215 A | 6/1997 | Boschetti et al. | |
| 5,648,100 A | 7/1997 | Boschetti et al. | |
| 5,662,935 A | 9/1997 | Motta | |
| 5,759,578 A | 6/1998 | Soon-Shiong et al. | |
| 5,879,709 A | 3/1999 | Soon-Shiong et al. | |
| 5,906,997 A | 5/1999 | Schwartz et al. | |
| 5,922,357 A | 7/1999 | Coombes et al. | |
| 6,087,450 A | 7/2000 | Breitbach et al. | |
| 6,218,440 B1 | 4/2001 | Kitagawa | |
| 6,248,363 B1 | 6/2001 | Yoshikawa et al. | |
| 6,306,922 B1 | 10/2001 | Hubbell et al. | |
| 6,309,669 B1 | 10/2001 | Setterstrom et al. | |
| 6,403,569 B1 | 6/2002 | Achterrath | |
| 6,548,081 B2 | 4/2003 | Sadozai et al. | |
| 6,555,138 B1 | 4/2003 | Karlsson et al. | |
| 6,569,463 B2 | 5/2003 | Patel et al. | |
| 6,689,374 B2 | 2/2004 | Chu et al. | |
| 6,790,456 B2 | 9/2004 | Vogel et al. | |
| 6,794,370 B2 | 9/2004 | Achterrath | |
| 6,923,988 B2 | 8/2005 | Patel et al. | |
| 6,946,146 B2 | 9/2005 | Muyle | |
| 7,070,809 B2 | 7/2006 | Goupil et al. | |
| 7,094,369 B2 | 8/2006 | Buiser et al. | |
| 7,144,588 B2 | 12/2006 | Oray et al. | |
| 7,153,572 B2 | 12/2006 | Cooper et al. | |
| 7,442,385 B2 | 10/2008 | Lewis et al. | |
| 7,449,236 B2 | 11/2008 | Lanphere et al. | |
| 7,462,366 B2 | 12/2008 | Lanphere et al. | |
| 7,588,780 B2 | 9/2009 | Buiser et al. | |
| 7,591,993 B2 | 9/2009 | Boschetti | |
| 7,670,592 B2 | 3/2010 | Boschetti | |
| 7,736,671 B2 | 6/2010 | DiCarlo et al. | |
| 7,776,240 B2 | 8/2010 | Chu et al. | |
| 7,794,755 B2 | 9/2010 | Figuly et al. | |
| 7,838,035 B2 | 11/2010 | Figuly | |
| 7,838,699 B2 | 11/2010 | Schwarz et al. | |
| 7,842,377 B2 | 11/2010 | Lanphere et al. | |
| 7,858,119 B1 | 12/2010 | Odidi et al. | |
| 7,887,846 B2 | 2/2011 | Figuly | |
| 7,897,179 B2 | 3/2011 | Muyle | |
| 7,951,402 B2 | 5/2011 | Lanphere et al. | |
| 8,062,673 B2 | 11/2011 | Figuly et al. | |
| 8,110,226 B2 | 2/2012 | Li | |
| 8,143,042 B2 | 3/2012 | Bettinger et al. | |
| 8,182,807 B2 | 5/2012 | Labhasetwar et al. | |
| 8,201,689 B2 | 6/2012 | Kaem | |
| 8,226,926 B2 | 7/2012 | Reb | |
| 8,252,302 B2 | 8/2012 | Macdonald | |
| 8,323,698 B2 | 12/2012 | Gu et al. | |
| 8,323,794 B2 | 12/2012 | Chu et al. | |
| 8,329,224 B2 | 12/2012 | Hall et al. | |
| 8,367,099 B2 | 2/2013 | Herweck et al. | |
| 8,383,758 B2 | 2/2013 | Papisov | |
| 8,426,481 B2 | 4/2013 | Hassleholm et al. | |
| 8,617,132 B2 | 12/2013 | Golzarian et al. | |
| 8,673,266 B2 | 3/2014 | Boschetti | |
| 8,691,791 B2 | 4/2014 | Lewis et al. | |
| 8,697,137 B2 | 4/2014 | Vogel et al. | |
| 8,709,384 B2 | 4/2014 | Reb | |
| 8,739,978 B2 | 6/2014 | Yoon et al. | |
| 8,741,351 B2 | 6/2014 | Vogel et al. | |
| 9,546,236 B2 * | 1/2017 | Cruise | C08F 220/56 |
| 9,803,043 B2 * | 10/2017 | Cruise | C08F 220/56 |
| 9,938,367 B2 * | 4/2018 | Cruise | A61K 9/0029 |
| 10,118,980 B1 | 11/2018 | Plotkin et al. | |
| 10,144,793 B2 * | 12/2018 | Cruise | A61K 9/1635 |
| 10,155,064 B2 | 12/2018 | Cruise et al. | |
| 10,400,051 B2 * | 9/2019 | Cruise | A61K 9/1635 |
| 10,543,295 B2 | 1/2020 | Cruise et al. | |
| 2002/0028243 A1 | 3/2002 | Masters | |
| 2002/0068089 A1 | 6/2002 | Vogel et al. | |
| 2002/0071855 A1 | 6/2002 | Sadozai et al. | |
| 2002/0197326 A1 | 12/2002 | Vogel et al. | |
| 2003/0078339 A1 | 4/2003 | Kiser et al. | |
| 2003/0183962 A1 | 10/2003 | Buiser et al. | |
| 2003/0206864 A1 | 11/2003 | Mangin | |
| 2004/0161466 A1 | 8/2004 | Lewis et al. | |
| 2005/0196702 A1 | 9/2005 | Bryant et al. | |
| 2005/0267556 A1 | 12/2005 | Shuros et al. | |
| 2006/0025560 A1 | 2/2006 | Inoue et al. | |
| 2006/0057098 A1 | 3/2006 | Sato | |
| 2006/0069168 A1 | 3/2006 | Tabata et al. | |
| 2006/0222596 A1 | 10/2006 | Askari et al. | |
| 2006/0240435 A1 | 10/2006 | Minoura et al. | |
| 2006/0251582 A1 | 11/2006 | Reb | |
| 2007/0035296 A1 | 2/2007 | Potapov et al. | |
| 2007/0213683 A1 | 9/2007 | Cassingham et al. | |
| 2007/0237741 A1 | 10/2007 | Figuly et al. | |
| 2007/0237742 A1 | 10/2007 | Figuly et al. | |
| 2007/0237830 A1 | 10/2007 | Figuly | |
| 2007/0237956 A1 | 10/2007 | Figuly et al. | |
| 2008/0033366 A1 | 2/2008 | Matson et al. | |
| 2008/0039890 A1 | 2/2008 | Matson et al. | |
| 2008/0102029 A1 | 5/2008 | Fritz et al. | |
| 2008/0113029 A1 | 5/2008 | Fritz et al. | |
| 2008/0220077 A1 | 9/2008 | Vogel et al. | |
| 2009/0029077 A1 | 1/2009 | Atanasoska et al. | |
| 2009/0092677 A1 | 4/2009 | Richard | |
| 2009/0117033 A1 | 5/2009 | O'Gara | |
| 2009/0164013 A1 | 6/2009 | Cruise et al. | |
| 2009/0246275 A1 | 10/2009 | O'Gara et al. | |
| 2009/0253809 A1 | 10/2009 | Gomurashvili et al. | |
| 2010/0028260 A1 | 2/2010 | Fritz et al. | |
| 2010/0040688 A1 | 2/2010 | Elbert et al. | |
| 2010/0057027 A1 | 3/2010 | Furno et al. | |
| 2010/0166876 A1 | 7/2010 | Lewis et al. | |
| 2010/0247667 A1 | 9/2010 | Ariga et al. | |
| 2010/0261646 A1 | 10/2010 | Lavik et al. | |
| 2011/0009327 A1 | 1/2011 | Hill et al. | |
| 2011/0009520 A1 | 1/2011 | Figuly et al. | |
| 2011/0033548 A1 | 2/2011 | Lai et al. | |
| 2011/0033608 A1 | 2/2011 | Figuly et al. | |
| 2011/0038936 A1 | 2/2011 | Griswold et al. | |

(56) References Cited

U.S. PATENT DOCUMENTS

| | | |
|---|---|---|
| 2011/0082427 A1 | 4/2011 | Golzarian et al. |
| 2011/0091550 A1 | 4/2011 | Zhang et al. |
| 2011/0152765 A1 | 6/2011 | Weber et al. |
| 2011/0182998 A1 | 7/2011 | Reb et al. |
| 2011/0212179 A1 | 9/2011 | Liu |
| 2012/0129798 A1 | 5/2012 | Akala et al. |
| 2012/0135170 A1 | 5/2012 | Meldal et al. |
| 2012/0213831 A1 | 8/2012 | Vogel et al. |
| 2012/0276151 A1 | 11/2012 | Lewis et al. |
| 2012/0289995 A1 | 11/2012 | Constant et al. |
| 2012/0302654 A1 | 11/2012 | Cruise et al. |
| 2013/0052142 A1 | 2/2013 | Harder et al. |
| 2013/0190795 A1 | 7/2013 | Matson et al. |
| 2013/0315838 A1 | 11/2013 | Reb et al. |
| 2013/0323306 A1 | 12/2013 | Weber |
| 2014/0030350 A1* | 1/2014 | Ashrafi .............. A61K 31/197 424/501 |
| 2014/0162969 A1 | 6/2014 | Lewis et al. |
| 2014/0186601 A1 | 7/2014 | Chang et al. |
| 2015/0079328 A1 | 3/2015 | Cruise et al. |
| 2015/0079395 A1 | 3/2015 | Cruise et al. |
| 2015/0166696 A1 | 6/2015 | Plotkin et al. |
| 2015/0306227 A1 | 10/2015 | Cruise et al. |
| 2016/0279282 A1 | 9/2016 | Cruise et al. |
| 2016/0311990 A1 | 10/2016 | Cruise et al. |
| 2017/0081450 A1 | 3/2017 | Cruise et al. |
| 2018/0085487 A1 | 3/2018 | Cruise et al. |
| 2018/0085497 A1 | 3/2018 | Hincapie et al. |
| 2019/0031798 A1 | 1/2019 | Plotkin et al. |
| 2019/0062479 A1 | 2/2019 | Cruise et al. |
| 2019/0076571 A1 | 3/2019 | Cruise et al. |
| 2019/0134257 A1 | 5/2019 | Hincapie et al. |
| 2019/0194406 A1 | 6/2019 | Cruise et al. |
| 2019/0255213 A1 | 8/2019 | Cruise et al. |

FOREIGN PATENT DOCUMENTS

| | | |
|---|---|---|
| EP | 1534351 B1 | 10/2006 |
| EP | 1820495 A2 | 8/2007 |
| EP | 1267839 B1 | 10/2007 |
| EP | 2269580 A2 | 1/2011 |
| EP | 2295480 A1 | 3/2011 |
| EP | 1796644 B1 | 4/2011 |
| EP | 1986706 B1 | 8/2011 |
| EP | 2368581 A2 | 9/2011 |
| EP | 2475695 B1 | 4/2014 |
| EP | 2286799 B1 | 7/2015 |
| JP | H05-279416 A | 10/1993 |
| JP | 2003-245544 A | 9/2003 |
| JP | 2011-201031 A | 10/2011 |
| JP | 2011-245267 A | 12/2011 |
| JP | 2012-100680 A | 5/2012 |
| JP | 2012-170773 A | 9/2012 |
| JP | 2012-187308 A | 10/2012 |
| JP | 2014-218439 A | 11/2014 |
| WO | 1995/019186 A2 | 7/1995 |
| WO | 2001/072281 A2 | 10/2001 |
| WO | 2002/015913 A1 | 2/2002 |
| WO | 2002/071994 A1 | 9/2002 |
| WO | 2003/094930 A1 | 11/2003 |
| WO | 2006/081517 A2 | 8/2006 |
| WO | 2006/119968 A2 | 11/2006 |
| WO | 2007/035296 A2 | 3/2007 |
| WO | 2007/133020 A1 | 11/2007 |
| WO | 2008/034911 A1 | 3/2008 |
| WO | 2008/047095 A1 | 4/2008 |
| WO | 2008/057163 A2 | 5/2008 |
| WO | 2008/128580 A1 | 10/2008 |
| WO | 2008/136536 A1 | 11/2008 |
| WO | 2009/015281 A2 | 1/2009 |
| WO | 2009/040434 A1 | 4/2009 |
| WO | 2009/073193 A2 | 6/2009 |
| WO | 2009/130332 A1 | 10/2009 |
| WO | 2009/131982 A1 | 10/2009 |
| WO | 2010/063630 A2 | 6/2010 |
| WO | 2011/014722 A2 | 2/2011 |
| WO | 2011/029867 A1 | 3/2011 |
| WO | 2011/068455 A1 | 6/2011 |
| WO | 2012/073188 A1 | 6/2012 |
| WO | 2012/120138 A1 | 9/2012 |
| WO | 2012/121073 A1 | 9/2012 |
| WO | 2012/133737 A1 | 10/2012 |
| WO | 2012/145431 A2 | 10/2012 |
| WO | 2012/166594 A1 | 12/2012 |
| WO | 2013/130143 A2 | 9/2013 |
| WO | 2013/177364 A1 | 11/2013 |
| WO | 2014/034787 A1 | 3/2014 |
| WO | 2015/042461 A1 | 3/2015 |
| WO | 2015/042462 A1 | 3/2015 |
| WO | 2015/070094 A1 | 5/2015 |
| WO | 2015/167752 A1 | 11/2015 |
| WO | 2016/154592 A1 | 9/2016 |
| WO | 2018/064389 A1 | 4/2018 |
| WO | 2018/064390 A1 | 4/2018 |

OTHER PUBLICATIONS

International Search Report and Written Opinion dated Dec. 24, 2014 for International Application No. PCT/US2014/056647 filed on Sep. 19, 2014.

International Search Report and Written Opinion dated Feb. 27, 2015 for International Application No. PCT/US2014/064680 filed on Nov. 7, 2014.

International Search Report and Written Opinion dated Dec. 24, 2014 for International Application No. PCT/US2014/056644 filed on Sep. 19, 2014.

Kamitani et al., Design of cell-surface-retained polymers for artificial ligand display. ChemBioChem, 10(2):230-233 (2009).

Supplementary European Search Report dated Apr. 19, 2017 for European Application No. 14845609.

Supplementary European Search Report dated Apr. 6, 2017 for European Application No. 14845676.7.

International Search Report and Written Opinion dated Jun. 2, 2016 for International Application No. PCT/US2016/024340 filed on Mar. 25, 2016.

Tarasyuk et al., Investigation into the influence of organic modifiers and ultradispersed hybrid fillers on the structure and properties of glass-ceramic coatings prepared by the sol-gel method. Glass Physics and Chemistry, vol. 32, No. 4 pp. 439-447 (2006).

European Search Report and Search Opinion dated Jul. 10, 2017 for European Patent Application Serial No. 14859554.9.

International Search Report and Written Opinion dated Dec. 20, 2017 for International Application No. PCT/US2017/054118 filed on Sep. 28, 2017.

International Search Report and Written Opinion dated Feb. 27, 2018 for International Application No. PCT/US2017/054113 filed on Sep. 28, 2017.

U.S. Appl. No. 16/693,077, filed Nov. 22, 2019.
U.S. Appl. No. 16/717,965, filed Dec. 17, 2019.
U.S. Appl. No. 16/821,783, filed Mar. 17, 2020.

* cited by examiner

POLYMER PARTICLES

CROSS REFERENCE TO RELATED APPLICATIONS

This application is a continuation of U.S. patent application Ser. No. 16/175,609, filed Oct. 30, 2018, which is a continuation of U.S. patent application Ser. No. 15/910,976, filed Mar. 2, 2018 (now U.S. Pat. No. 10,144,793), which is a continuation of U.S. patent application Ser. No. 15/630,048, filed Jun. 22, 2017 (now U.S. Pat. No. 9,938,367), which is a is a continuation of U.S. patent application Ser. No. 15/369,213, filed Dec. 5, 2016 (now U.S. Pat. No. 9,803,043), which is a continuation of U.S. patent application Ser. No. 14/491,776, filed Sep. 19, 2014 (now U.S. Pat. No. 9,546,236), which claims the benefit of U.S. provisional patent application No. 61/880,036, filed Sep. 19, 2013, the entire disclosure each of which is incorporated herein by reference.

FIELD

Biodegradable polymer particles for the occlusion of vascular sites and cavities within the body, such as the embolization of hypervascularized tumors or arteriovenous malformations are described.

SUMMARY

Described herein generally are biodegradable, cross-linked polymer particles. In some embodiments, the particles can have a spherical shape or be substantially spherical. Thus, the particles described herein can be referred to as microshperes or polymer spheres. These polymers can be used for/in embolization. The polymer particles can include and/or be formed of one or more monomers and a cross-linker susceptible to chemical hydrolysis or enzymatic action.

The biodegradable polymer particles described herein can be utilized for the occlusion of vascular sites, bodily lumen, and other cavities within the body. In some embodiments, the polymer particles can be used for such purposes as the embolization of hypervascularized tumors or arteriovenous malformations.

Polymer particles can comprise: at least one monomer and at least one crosslinker. In some embodiments, the polymer particles can be susceptible to degradation through chemical hydrolysis or enzymatic action. Particles as described herein can have various sizes depending on a particular use, but generally can have diameters between about 40 µm and about 1,200 µm or between about 75 µm and about 1,200 µm.

Methods of making a polymer particle as described herein are also described. These methods comprise: preparing an aqueous prepolymer solution including at least one monomer, at least one crosslinker susceptible to degradation through chemical hydrolysis or enzymatic action, and an initiator; dispersing the aqueous prepolymer solution in mineral oil; and forming the polymer particles via polymerization of the monomers.

Other methods to form polymer particles can include: reacting a prepolymer solution in an oil to form the polymer particles. The prepolymer solution can include at least one monomer comprising at least one functional group, at least one crosslinker susceptible to degradation through chemical hydrolysis or enzymatic action, and an initiator.

The crosslinkers used to form the polymer particles can impart biodegradability to the particles. For example, the crosslinker can include at least one linkage susceptible to degradation through chemical hydrolysis or enzymatic action. The cross-linker can be glycidyl, glycidyl amino, thioester, or protein based. A glycidyl based crosslinker may be bis-glycidyl amino alcohol. A protein based crosslinker may be bi-functionalized methacryloyl-Ala-Pro-Gly-Leu-AEE-methacrylate.

DRAWINGS

DETAILED DESCRIPTION

Figure 1:
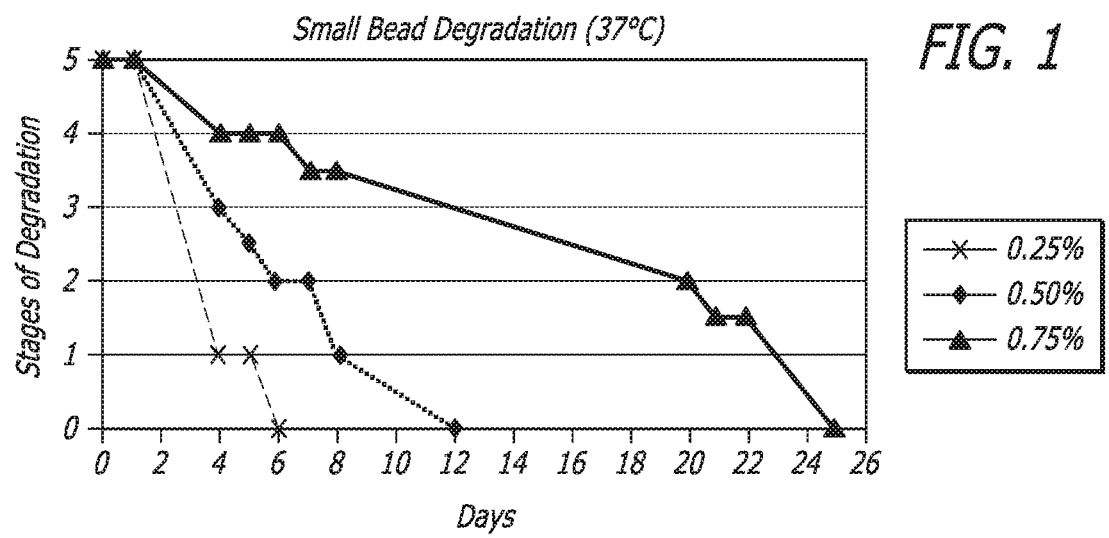
FIG. 1 is a graph showing the stages of degradation for different polymer particles.

Described herein generally are particles made of polymer material. The polymer material can be a reaction product of one or more monomers and a crosslinker. In some embodiments, the polymer particles can be susceptible to hydrolysis or enzymatic action. The particles can be referred to herein as being microparticles, microspheres and the like. The particles can have a diameter of between about 40 µm and about 1,200 µm or between about 75 µm and about 1,200 µm. The particles can also be compressible and/or durable for ease of delivery through a medical device such as a needle or catheter. The particles can also be biodegradable once delivered.

The particles can be formed from a mixture such as a prepolymer solution. The prepolymer solution can comprise: (i) one or more monomers that contain a singular functional group amenable to polymerization and (ii) one or more crosslinkers. In some embodiments, a polymerization initiator may be utilized.

In some embodiments, if one of the monomer(s) and/or crosslinker(s) is a solid, a solvent can be utilized in the preparation of the particles for use as embolics. If liquid monomers and crosslinkers are utilized, a solvent may not be required. In some embodiments, even when using liquid monomers and crosslinkers, a solvent may still be used. Solvents may include any liquid that can dissolve or substantially dissolve a monomer, monomer mixture, and/or a crosslinker. Any aqueous or organic solvent may be used that dissolves the desired monomer(s), crosslinker(s), and/or polymerization initiators. If an organic solvent is used, an aqueous media may be required for dispersion. In one embodiment, the solvent can be water. Additionally, solutes, e.g. sodium chloride, may be added to the solvent to increase the rate of polymerization. Solvent concentrations can be about 10% w/w, about 20% w/w, about 30% w/w, about 40% w/w, about 50% w/w, about 60% w/w, about 70% w/w, about 80% w/w, about 90% w/w, between about 20% w/w and about 80% w/w, between about 50% w/w and about 80% w/w, or between about 30% w/w and about 60% w/w of the solution.

Any type of crosslinking chemistry can be utilized to prepare the described polymer particles. In some embodiments, for example crosslinking chemistries such as, but not limited to nucleophile/N-hydroxysuccinimide esters, nucleophile/halide, vinyl sulfone/acrylate or maleimide/acrylate can be used. In one example embodiment, free radical polymerization can be used. As such, monomers with a singular ethylenically unsaturated group, such as acrylate, acrylamide, methacrylate, methacrylamide, and vinyl, may be used when employing free radical polymerization.

Any amount of monomer can be used that allows for a desired particle. Monomer concentration in the solvent can be about 1% w/w, about 2% w/w, about 3% w/w, about 4% w/w, about 5% w/w, about 10% w/w, about 15% w/w, about 20% w/w, about 30% w/w, about 40% w/w, about 50% w/w, about 60% w/w, about 70% w/w, about 80% w/w, about 90% w/w, about 100% w/w, between about 1% w/w and about 100% w/w, between about 40% w/w and about 60% w/w, between about 50% w/w and about 60% w/w, or between about 40% w/w and about 60% w/w.

Monomers can be selected based on imparting desired chemical and/or mechanical properties to the polymer particle or particle embolic. If desired, uncharged, reactive moieties can be introduced into the particle embolic. For example, hydroxyl groups can be introduced into the particle embolic with the addition of 2-hydroxyethyl acrylate, 2-hydroxymethacrylate, derivatives thereof, or combinations thereof. Alternatively, uncharged, relatively unreactive moieties can be introduced into the particle embolic. For example, acrylamide, methacrylamide, methyl methacrylate, derivatives thereof, or combinations thereof can be added.

In one embodiment, polymer particles can be prepared from monomers having a single functional group suitable for polymerization. Functional groups can include those suitable to free radical polymerization, such as acrylate, acrylamide, methacrylate, and methacrylamide. Other polymerization schemes can include, but are not limited to nucleophile/N-hydroxysuccinimide esters, nucleophile/halide, vinyl sulfone/acrylate or maleimide/acrylate. Selection of the monomers is governed by the desired mechanical properties of the resulting particle and minimizing the biological effects of degradation products.

In some embodiments, the monomer can additionally contain an ionizable functional group that is basic (e.g. amines, derivatives thereof, or combinations thereof). The amine group may be protonated at pH's less than the pKa of the amine, and deprotonated at pH's greater than the pKa of the amine. In other embodiments, the monomer additionally contains an ionizable functional group that is acidic (e.g. carboxylic acids, sulfonic acids, derivatives thereof, or combinations thereof). The acid group may be deprotonated at pHs greater than the pKa of the acid, and protonated at pHs less than the pKa of the acid.

If the binding of positively charged drugs is desired, monomers with negatively charged moieties, e.g. carboxylic acids, or other acidic moieties can be polymerized into the particle embolic. Acidic, ionizable, ethylenically unsaturated monomers can include, but are not limited to, acrylic acid, methacrylic acid, 3-sulfopropyl acrylate, 3-sulfopropyl methacrylate, derivatives thereof, combinations thereof, and salts thereof. On the other hand, if the binding of negatively charged drugs is desired, monomers with positively charged moieties, e.g. amines, or other basic moieties can be included. Basic, ionizable, ethylenically unsaturated monomers can include, but are not limited to amino ethyl methacrylate, aminopropyl methacrylate, derivatives thereof, combinations thereof, and salts thereof.

An additional factor in monomer selection can be the desire for degradation products of the particle embolic to elicit a negligible response from the host. In other embodiments, there can be desire for degradation products of the particles to elicit substantially no response from the host.

A crosslinker can include one or more polymerizable groups, can join monomer chains together, and permit the formation of solid particles. Biodegradation can be imparted to the particle embolic by utilizing a crosslinker with linkages susceptible to degradation in a physiological environment. Over time in vivo, linkages can break and the polymer chains may no longer be bound together. The judicious selection of monomers permits the formation of water-soluble degradation products that diffuse away and are cleared by the host. Linkages susceptible to hydrolysis, such as esters, thioesters, carbamates, and carbonates, or peptides degraded by enzymes can be used in biodegradable products.

In one embodiment, one or more crosslinkers can contain at least two functional groups suitable for polymerization and at least one linkage susceptible to breakage to impart biodegradation to the polymer particle. Linkages susceptible to breakage in a physiological environment can include, but are not limited to those susceptible to hydrolysis, including esters, thioesters, carbamates, and carbonates, and those susceptible to enzymatic action, including peptides that are cleaved by matrix metalloproteinases, collagenases, elastases, and cathepsins. In some embodiments, multiple crosslinkers can be utilized to control degradation rate in a manner not possible with only one crosslinker. In one embodiment, at least one crosslinker is susceptible to hydrolysis and at least one crosslinker is susceptible to enzymatic degradation.

In some embodiments, the at least one linkage is a peptide cleavable by matrix metalloproteinases, a peptide cleavable by matrix collagenases, a peptide cleavable by matrix elastases, a peptide cleavable by matrix cathepsins, or a combination thereof.

In other embodiments, the polymers can include a second crosslinker including a second linkage selected from an ester, a thioester, a carbonate, a carbamate, a peptide cleavable by matrix metalloproteinases, a peptide cleavable by matrix collagenases, a peptide cleavable by matrix elastases, and a peptide cleavable by matrix cathepsins.

In still other embodiments, the polymers can include a third, fourth, fifth or more crosslinkers each including the same or a different linkage.

Crosslinkers can include peptide based crosslinkers, carbonate based crosslinkers, bis glycidyl amine crosslinkers, TMP gly ester crosslinkers, di thio ester crosslinkers, or jeffamine glycidyl amine crosslinkers. Preferred concentrations of the crosslinkers in the final product can be about 0.05% w/w, about 0.1% w/w, about 0.5% w/w, about 1.0% w/w, about 2.0% w/w, about 3.0% w/w, about 4.0% w/w, between about 0.1% w/w and about 4.0% w/w, between about 0.5% w/w and about 2% w/w, or between about 1% w/w and about 1.5% w/w. A skilled artisan understands how to calculate final concentrations based on the amount in solvent already discussed.

In one embodiment, crosslinkers can be peptide based compounds. In one embodiment, a peptide based crosslinker can be

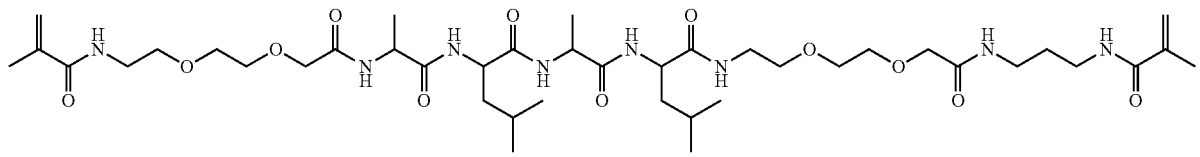 [SMILES: C=C(C)C(=O)NCCCNC(=O)COCCOCCNC(=O)C(CC(C)C)NC(=O)C(C)NC(=O)C(CC(C)C)NC(=O)C(C)NC(=O)COCCOCCNC(=O)C(=C)C]

or a derivative thereof.

In another embodiment, the peptide based crosslinker can be

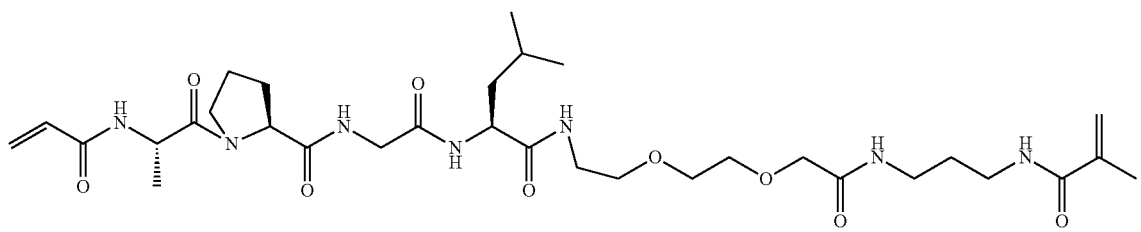 [SMILES: C=CC(=O)N[C@@H](C)C(=O)N1CCC[C@H]1C(=O)NCC(=O)N[C@@H](CC(C)C)C(=O)NCCOCCOCC(=O)NCCCNC(=O)C(=C)C]

or a derivative thereof.

In another embodiment, the peptide based crosslinker can be bi-functionalized methacryloyl-Ala-Pro-Gly-Leu-AEE-methacrylate.

In another embodiment, crosslinkers can have a structure

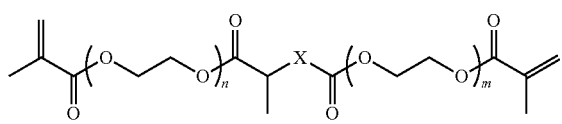

wherein n is 1 to 20;
m is 1 to 20; and
X is O or S.

In another embodiment, the crosslinker can have a structure

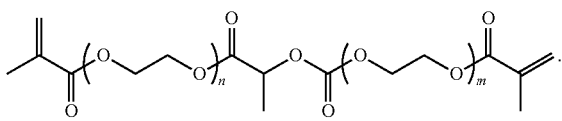

wherein n is 1 to 20;
m is 1 to 20.

In another embodiment, the crosslinker can have a structure

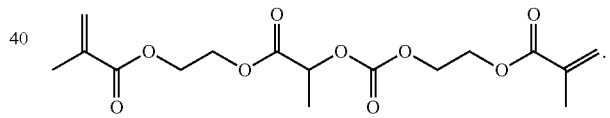

A crosslinker can also have a structure

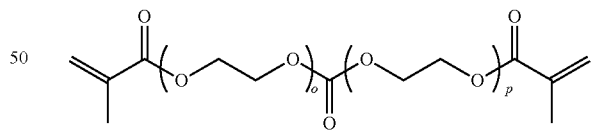

wherein o is 1 to 20; and
p is 1 to 20.

In one embodiment, the structure can be

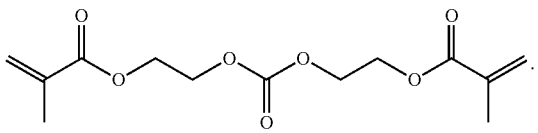 [SMILES: C=C(C)C(=O)OCCOC(=O)OCCOC(=O)C(=C)C]

A crosslinker can further have a structure

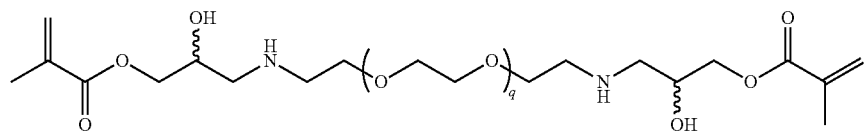

wherein q is 1 to 10. In one embodiment, q is 1.

A crosslinker can further have a structure

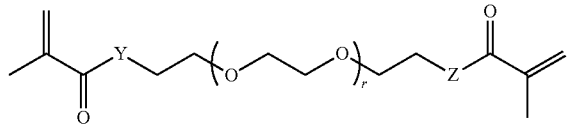

wherein r is 1 to 20; and
Y and Z are each independently selected from O, S, and NH.

In one embodiment, the crosslinker can have a structure

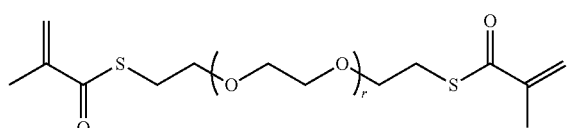

or

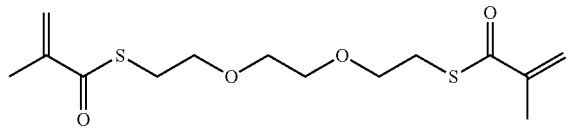

wherein r is 1 to 20.

Further, in another embodiment, the crosslinker can have a structure

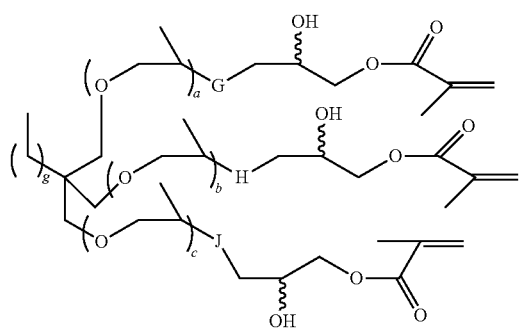

wherein G, H and J are each independently CH$_2$, O, S, NH, or not present,
a, b, and c are each independently 1 to 20; and
g is 1 to 20.

In another embodiment, a, b, and c are each independently 1 to 10. In still another embodiment, G, H and J are each independently O or NH.

In one embodiment, the crosslinker has a structure

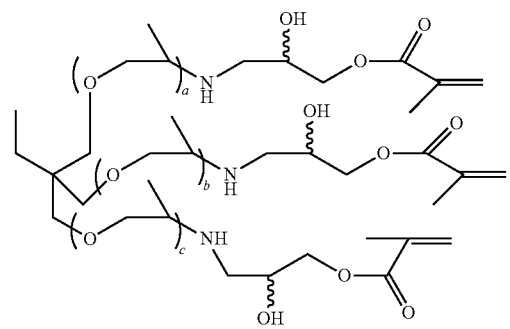

wherein a, b, and c are each independently 1 to 20.

Further, in another embodiment, the crosslinker can have a structure

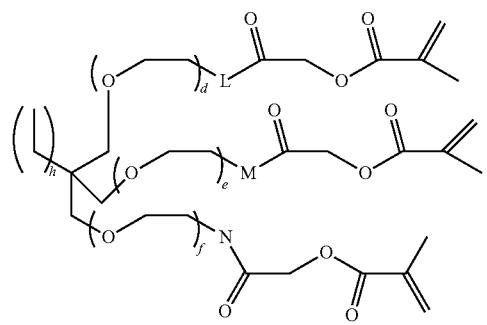

wherein L, M and N are each independently CH$_2$, O, S, NH, or not present,
d, e, and f are each independently 1 to 20; and
h is 1 to 20.

In another embodiment, d, e, and f are each independently 1 to 10. In still another embodiment, L, M and N are each independently O or NH.

In one embodiment, the crosslinker has a structure

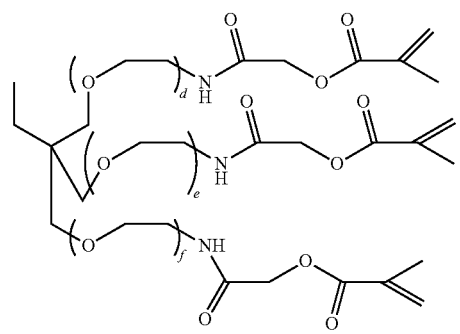

wherein d, e, and f are each independently 1 to 20.

A crosslinker can also have a structure

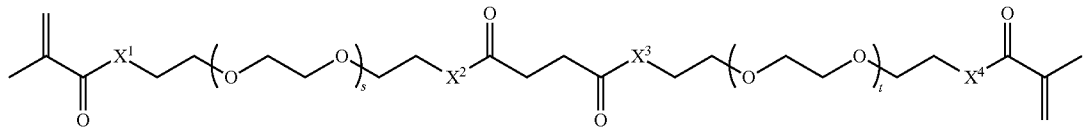

wherein s is 1 to 20;
wherein t is 1 to 20; and
$X^1$, $X^2$, $X^3$ and $X^4$ are each independently O or S.

In one embodiment, the structure can be

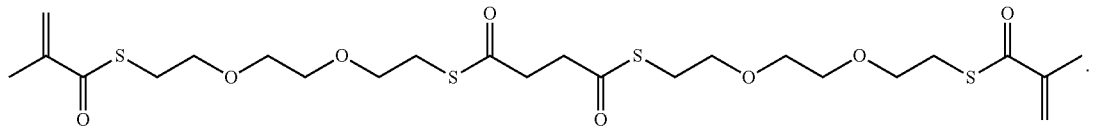 [SMILES: C=C(C)C(=O)SCCOCCOCCSC(=O)CCC(=O)SCCOCCOCCSC(=O)C(=C)C]

A crosslinker can also have a structure

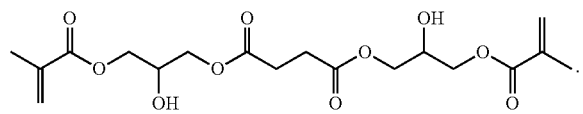 [SMILES: C=C(C)C(=O)OCC(O)COC(=O)CCC(=O)OCC(O)COC(=O)C(=C)C]

In some embodiments, a crosslinker can be a tetra ester, a tetra thioester or a dithio ester. In other embodiments, the crosslinker can be a peptide crosslinker or a carbonate crosslinker. A glycidyl based crosslinker may be bis-glycidyl amino alcohol.

Polymerization of the prepolymer solution can be by reduction-oxidation, radiation, heat, or any other method known in the art. Radiation cross-linking of the prepolymer solution can be achieved with ultraviolet light or visible light with suitable initiators or ionizing radiation (e.g. electron beam or gamma ray) without initiators. Cross-linking can be achieved by application of heat, either by conventionally heating the solution using a heat source such as a heating well, or by application of infrared light to the monomer solution. The free radical polymerization of the monomer(s) and crosslinker(s) is preferred and requires an initiator to start the reaction. In a preferred embodiment, the cross-linking method utilizes azobisisobutyronitrile (AIBN) or another water soluble AIBN derivative such as (2,2'-azobis (2-methylpropionamidine)dihydrochloride). Other cross-linking agents can include, but are not limited to N,N,N', N'-tetramethylethylenediamine, ammonium persulfate, benzoyl peroxides, and combinations thereof, including azobisisobutyronitriles. A preferred initiator can be a combination of N,N,N',N'-tetramethylethylenediamine and ammonium persulfate.

Polymer particles can be produced or formed by methods including: reacting a prepolymer solution including at least one monomer including at least one functional group, at least one crosslinker susceptible to degradation through chemical hydrolysis or enzymatic action, and an initiator in an oil.

The prepolymer solution can be prepared by dissolving the monomer(s), crosslinker(s), and optionally initiator(s) in the solvent. The particle embolics can be prepared by emulsion polymerization. A non-solvent for the monomer solution, typically mineral oil when the monomer solvent is water, is sonicated to remove any entrapped oxygen. The mineral oil and a surfactant are added to the reaction vessel. An overhead stirrer is placed in the reaction vessel. The reaction vessel is then sealed, degassed under vacuum, and sparged with an inert gas such as argon. The initiator component N,N,N',N'-tetramethylethylenediamine is added to the reaction vessel and stirring commenced. Ammonium persulfate is added to the polymerization solution and both are then added to the reaction vessel, where the stirring suspends droplets of the prepolymer solution in the mineral oil.

The rate of stirring can affect particle size, with faster stirring producing smaller particles. Stirring rates can be about 100 rpm, about 200 rpm, about 300 rpm, about 400 rpm, about 500 rpm, about 600 rpm, about 700 rpm, about 800 rpm, about 900 rpm, about 1,000 rpm, about 1,100 rpm, about 1,200 rpm, about 1,300 rpm, between about 200 rpm and about 1,200 rpm, between about 400 rpm and about 1,000 rpm, at least about 100 rpm, at least about 200 rpm, at most about 1,300 rpm, or at most about 1,200 rpm to produce particles with desired diameters.

The polymer particles described herein can have a generally or substantially spherical shape. The substantially spherical or spherical particles can have diameters of about 10 µm, about 20 µm, about 30 µm, about 40 µm, about 50 µm, about 60 µm, about 75 µm, about 100 µm, about 200 µm, about 300 µm, about 400 µm, about 500 µm, about 600 µm, about 700 µm, about 800 µm, about 900 µm, about 1,000 µm, about 1,100 µm, about 1,200 µm, about 1,300 µm, about 1,400 µm, about 1,500 µm, about 1,600 µm, between about 50 µm and about 1,500 µm, between about 100 µm and about 1,000 µm, between about 75 µm and about 1,200 µm, at least about 50 µm, at least about 80 µm, at most about 1,500 µm, or at most about 1,200 µm. In some embodiments, the diameter can be between about 40 µm and about 1,200 µm, between about 40 µm and about 60 µm, or between about 75 µm and about 1,200 µm.

The polymer particles can retain their diameters even after injection through a catheter or other delivery device. In other words, the polymer particles may not fall apart or otherwise fracture during delivery. In some embodiments, the polymer particles can retain about 99%, about 98%, about 97%, about 96%, about 95%, about 90%, greater than about 99%, greater than about 98%, greater than about 97%, greater than about 96%, greater than about 95%, greater than about 90%, between about 90% and about 100% of their diameter after delivery.

The polymer particles can also have a characteristic circularity or have a relative shape that is substantially circular. This characteristic describes or defines the form of a region on the basis of its circularity. Polymer particles as described herein can have a fraction of circularity of about 0.8, 0.9, 0.95, 0.96, 0.97, 0.98, 0.99, greater than about 0.8, greater than about 0.9, or greater than about 0.95. In one embodiment, the circularity of the polymer particles is greater than about 0.9.

The polymer particles can retain their circularity even after injection through a catheter or other delivery device. In some embodiments, the polymer particles can retain about 99%, about 98%, about 97%, about 96%, about 95%, about 90%, greater than about 99%, greater than about 98%, greater than about 97%, greater than about 96%, greater than about 95%, greater than about 90%, between about 90% and about 100% of their circularity after delivery.

Polymerization can be allowed to proceed as long as necessary to produce particles with desired resiliency. Polymerization can be allowed to proceed for about 1 hr, 2 hr, 3 hr, 4 hr, 5 hr, 6 hr, 7 hr, 8 hr, 9 hr, 10 hr, 11 hr, 12 hr, 18 hr, 24 hr, 48 hr, 72 hr, 96 hr, between about 1 hr and about 12 hr, between about 1 hr and about 6 hr, between about 4 hr and about 12 hr, between about 6 hr and about 24 hr, between about 1 hr and about 96 hr, between about 12 hr and about 72 hr, or at least about 6 hours.

Polymerization can be run at a temperature to produce particles with desired resiliency and/or reaction time. Polymerization can be run at a temperature of about 10° C., about 20° C., about 30° C., about 40° C., about 50° C., about 60° C., about 70° C., about 80° C., about 90° C., about 100° C., between about 10° C. and about 100° C., between about 10° C. and about 30° C., at least about 20° C., at most about 100° C., or at about room temperature. In one embodiment, polymerization occurs at room temperature.

After the polymerization is complete, the polymer particles are washed to remove any solute, mineral oil, unreacted monomer(s), and/or unbound oligomers. Any solvent may be utilized, but care should be taken if aqueous solutions are used to wash particles with linkages susceptible to hydrolysis. Preferred washing solutions can include, but are not limited to acetone, alcohols, water and a surfactant, water, saline, buffered saline, and saline and a surfactant.

Optionally, the washed polymer particles can then be dyed to permit visualization before injection into a microcatheter. A dye bath can be made by dissolving sodium carbonate and the desired dye in water. Particle embolics are added to the dye bath and stirred. After the dying process, any unbound dye is removed through washing. After dying and washing, the particles can be packaged into vials or syringes, and sterilized.

After the preparation of the particle embolics, they can be optionally dyed to permit visualization during preparation by the physician. Any of the dyes from the family of reactive dyes which bond covalently to the particle embolics can be used. Dyes can include, but are not limited to, reactive blue 21, reactive orange 78, reactive yellow 15, reactive blue No. 19, reactive blue No. 4, C.I. reactive red 11, C.I. reactive yellow 86, C.I. reactive blue 163, C.I. reactive red 180, C.I. reactive black 5, C.I. reactive orange 78, C.I. reactive yellow 15, C.I. reactive blue No. 19, C.I. reactive blue 21, or any of the color additives. Some color additives are approved for use by the FDA part 73, subpart D. In other embodiments, a dye that can irreversibly bond to the polymer matrix of the particle embolic may be used.

If the herein described polymer particle or microsphere does not adequately bind any of the reactive dyes described above, a monomer containing an amine can be added to the monomer solution in an amount to achieve the desired coloration. Even if the polymer particle or microsphere does adequately bind the reactive dyes described above, a monomer containing an amine can be added to the monomer solution. Examples of suitable amine containing monomers include aminopropyl methacrylate, aminoethyl methacrylate, aminopropyl acrylate, aminoethyl acrylate, derivatives thereof, combinations thereof, and salts thereof. Preferred concentrations of the amine containing monomers in the final product can be less than or equal to about 1% w/w.

The particles described herein can be sterilized without substantially degrading the polymer. After sterilization, at least about 50%, about 60%, about 70%, about 80%, about 90%, about 95% about 99% or about 100% of the polymer can remain intact. In one embodiment, the sterilization method can be autoclaving and can be utilized before administration.

The final polymer particle preparation can be delivered to the site to be embolized via a catheter, microcatheter, needle, or other similar delivery device. A radiopaque contrast agent can be thoroughly mixed with the particle preparation in a syringe and injected through a catheter until blood flow is determined to be occluded from the site by interventional imaging techniques.

In some embodiments, it may be desirable for the particles to degrade over time. In other words, the particles can be degradable and/or biodegradable. In such embodiments, the particles can degrade to less than about 40%, about 30% about 20%, about 10%, about 5% or about 1% intact after about 2 days, 3 days, 5 days, about 2 weeks, about 1 month, about 2 months, about 6 months, about 9 months, about a year, about 2 years, about 5 years, or about 10 years. In one embodiment, the particles can be substantially degraded in less than about 1 month. In another embodiment, the particles can be substantially degraded in less than about 6 months.

In some embodiments, degradability can be accelerated with an appropriate and/or adequate enzyme. In some embodiments, the polymer particles can be injected along with an enzyme that can accelerate the degradation of the particles. In other embodiments, an enzyme can be delivered to the site of the implanted particles at a remote time and accelerate degradation at that time.

In some embodiments, the greater the percentage of a crosslinker in the final polymer particles, the longer degradation takes. Additionally, the larger the particle diameter, the longer the degradation. Thus, the particles with the longest degradation time are those that have the largest concentration of crosslinker and the largest diameter. These two properties can be varied to tailor degradation time as needed.

The polymer particles described herein can be compressible yet durable enough not to break apart or fragment. Substantially no change in circularity or diameter of particles occurs during delivery through a microcatheter. In other words, after delivery through a microcatheter, the polymer particles described herein remain greater than about 60%, about 70% about 80%, about 90%, about 95%, about 99% or about 100% intact after delivery.

Further, in some embodiments, the particles can stick to the tissue and/or remain in place through friction with the tissues. In other embodiments, the particles can act as a plug in a vessel held in place by the flow and pressure of the blood itself. In still other embodiments, the particles can be cohesive enough to stick to one another to aid in agglomerating particles at a particular site of action.

Polymer particles described can be delivered through a microcatheter or other appropriate delivery device to a remote tissue or can be injected through a needle to local tissues. The polymer particles can be used for occlusion of vascular sites and cavities within the body.

In some embodiments, the polymer particles can be configured for embolization of hypervascularized tumors or arteriovenous malformations. In some embodiments, a patient can be selected that exhibits a hypervascularized tumor and/or an arteriovenous malformation. A microcatheter can be navigated to the location of the tumor or malformation. Polymer particles as described herein can be injected into that site to stabilize it thereby treating the patient's condition.

Example 1

Preparation of a Glycidyl-Based Crosslinker

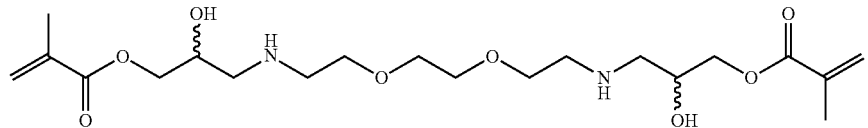 [SMILES: C=C(C)C(=O)OCC(O)CNCCOCCOCCNCC(O)COC(=O)C(=C)C]

A 10 g (67.6 mmol) aliquot of 2,2'-(ethylenedioxy)bis(ethylamine) was mixed with 10 g (70.4 mmol) of glycidyl methacrylate, and 3 g of silica gel (Aldrich 645524, 60 Angstrom, 200-425 mesh). After stirring for 1 hr, another 9 g (63.4 mmol) of glycidyl methacrylate was added and the suspension was stirred for an additional 1.5 hr. The mixture was diluted with 200 mL chloroform and filtered through a 600 mL fritted glass Buchner funnel to remove the silica gel. LC-MS analysis of the resultant chloroform solution showed no mono glycidyl amino alcohol and mainly bis-glycidyl amino alcohol at [M+H]+ m/z 433.2. The solution was concentrated to about 50 g in vacuo. The resultant heavy syrup was diluted to 100 mL with acetonitrile and stored at −80° C.

Example 2

Preparation of a Peptide-Based Crosslinker

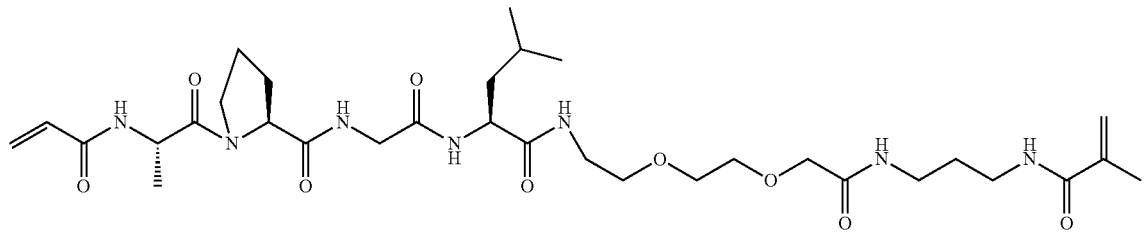 [SMILES: C=CC(=O)N[C@@H](C)C(=O)N1CCC[C@H]1C(=O)NCC(=O)N[C@@H](CC(C)C)C(=O)NCCOCCOCC(=O)NCCCNC(=O)C(=C)C]

A heterobifunctional, tetrapeptide (Acryloyl-Ala-Pro-Gly-Leu-AEE-N-hydroxysuccinimide) was provided (Bachem, Torrance, Calif.). The peptide (653 mg, 1 mmol) was dissolved in 5 mL DMF and N-(3-aminopropyl)methacrylamide hydrochloride (190 mg, 1.1 mmol) and N,N-diisopropylethylamine (174 μL, 1 mmol) were added. After 2 hr, 20 mg of butylated hydroxytoluene was added and the reaction mixture was exposed to air. The reaction mixture was precipitated with 200 mL of ethyl ether. The solids were collected using centrifugation. The pellet was re-dissolved in a 90/5/5 solution of chloroform/methanol/methanol+5% aqueous ammonia and applied to 50 g of silica gel in a 5×20 cm column (Aldrich, 60 Angstrom, 200-425 mesh). The silica gel column was developed with 500 mL of 90/5/5 solution of chloroform/methanol/methanol+5% aqueous ammonia and the peptide containing eluent was concentrated in vacuo to yield 110 mg of pale yellow oil. The pale yellow oil was dissolved in 10 mL methanol and stored at −80° C. LC-MS analysis of the product showed the desired [M+H]$^+$ at m/z 680 and [M+Na]$^+$ at m/z 702.

Example 3

MA-AEEAc-ALAL-AEEAc-MA, ALAL Tetrapeptide Crosslinker the reaction mixture and the residue was suspended in 500 mL of dry ether and collected by filtration onto a dry 600 mL Buchner funnel with a medium frit. After carefully rinsing the solids on the funnel with dry ether several times, the solids were dried in the vacuum oven overnight to give 45 g of a hygroscopic beige powder (Compound A) which has to quickly be placed into a dry environment.

HEMA-1-Chloroethyl carbonate: To 24 mL of HEMA (200 mmol) in 1000 mL of dry ether was added 16.8 mL (213 mmol) of pyridine at 4-10° C., under argon. To this solution was added 21.3 mL (200 mmol) of 1-chloroethyl chlorocarbonate, drop wise with stirring over 0.5 hour. After stirring 0.5 hr at 4-10° C., the heavy precipitate (Compound B) was removed by filtration and the filtrate was concentrated to an oil in vacuo, yielding 44 g (100%).

To 4.4 g (20 mmol) of Compound B in 40 mL of anhydrous dimethyl formamide, was added 0.9 g (4.0 mmol) of Compound A at 100° C., under argon, with good stirring. After 15 min, another 1.2 g (5.4 mmol) of Compound A was added at 100° C., under argon, with good stirring followed by a final 0.9 g (4.0 mmol), under the same conditions, for a total of 2.9 g Compound A (13.4 mmol). The yellow brown reaction mixture was heated at 100° C. for an additional 3 hr and after cooling to room temperature the solvent was removed in vacuo, and the residue was left on the vacuum

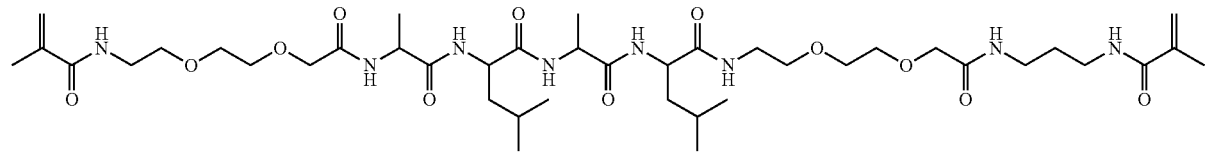 [SMILES: C=C(C)C(=O)NCCCNC(=O)COCCOCCNC(=O)C(CC(C)C)NC(=O)C(C)NC(=O)C(CC(C)C)NC(=O)C(C)NC(=O)COCCOCCNC(=O)C(=C)C]

To 841 mg (1 mmol) of NHS ester, MA-AEEAc-ALAL-AEEAc-NHS was added 179 mg of 3-aminopropyl methacrylate-HCl into a clean dry 15 mL flask with a dry stir bar and a dry septum, followed by 5 mL of dry dimethyl formamide. Upon stirring, a clear solution resulted and 200 μL (1 mmol) of diisopropylethylamine was added all at once. After one hour, the reaction mixture was transferred to a 250 mL pear shaped flask using 3×5 mL of methanol and placed on the vacuum (vac) line overnight. The next day the reaction mixture was transferred to a scintillation vial with 2 mL of methanol, to give approx. 35% solids, and stored at −80° C. The crude crosslinker above gives a single HPLC peak gives [M+H]$^+$ at m/z of 869.9, molecular mass calculated for $C_{41}H_{72}N_8O_{12}$ is 868.5.

Example 4

Carbonate Crosslinkers

To 33 g (100 mmol) of cesium carbonate suspended in 500 mL of 1:1 acetonitrile:methanol was added 17.2 g (200 mmol) of methacrylic acid over one hour with good stirring. After stirring an additional 2 hr, solvent was removed from line overnight. The residue was taken up in 50 mL of 1:1 chloroform:hexane, applied to a 750 gram gold column, and eluted with hexane and then 0-20% ethyl acetate in hexane. The following carbonate

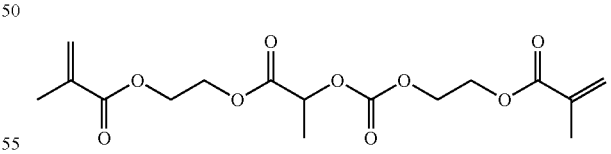

came out starting at 27 min and the following carbonate

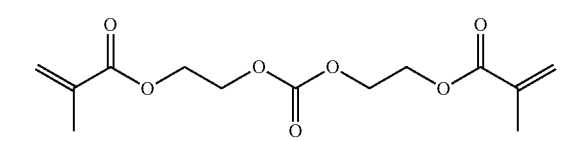 [SMILES: C=C(C)C(=O)OCCOC(=O)OCCOC(=O)C(=C)C]

came off at 32 min.

Example 5

TMP Gly Ester

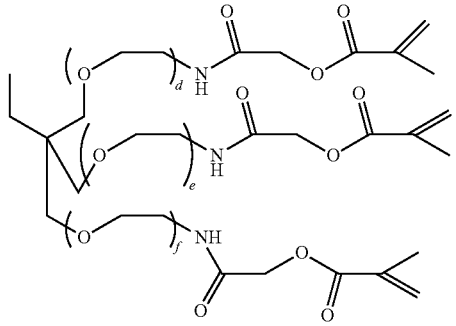

TMP-Chloroacetamide: To 13.2 g of triamino trimethylol propane ethoxylate in 250 mL of dry tetrahydrofuran (THF) was added 6.32 g (80 mmol) of pyridine and this solution was added to 6.44 g of chloroacetyl chloride in 250 mL of THF with good stirring, at 4-10° C. under argon (Ar). After stirring for 15 min, the reaction mixture was warmed to room temperature and the THF and other volatile material were removed in vacuo. The resulting solids were dissolved into 200 mL of chloroform which was in turn washed with 100 mL of saturated aqueous sodium bicarbonate, dried over magnesium sulfate and the solvent was removed in vacuo.

TMP-NH-Gly-Methacrylate: To approx 15 g of material above dissolved in 75 mL of anhydrous dimethyl formamide was added 18 g of cesium methacrylate and the resulting suspension heated at 40-50° C. for 2 hrs.

After precipitation with 500 mL of chloroform, the inorganic salts were collected by filtration and the filtrate was concentrated to an oil in vacuo to give 18 g of a reddish brown oil. This oil could be polymerized with AIBN at 80° C., in IPA to a hard pellet. Chromatography on 6 g of this through a plug of the above silica with 1200 mL of 2-20% methanol in chloroform, gave 6 g of light red colored material.

Example 6

Dithio Ester

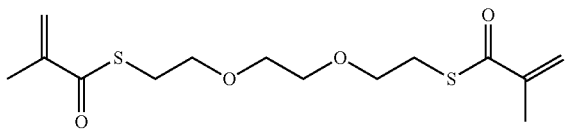 [SMILES: C=C(C)C(=O)SCCOCCOCCSC(=O)C(=C)C]

To 6.6 mL (40 mmol) of 2,2'-(ethylenedioxy)ethanedithiol in 200 mL of tetrahydrofuran (THF) was added 20.9 mL of diisopropylethyl amine and the resulting dry solution was added to 11.5 mL of methacryloyl chloride (120 mmol) in 200 mL of dry THF, at −5° C., with good stirring over 1 hr. The reaction mixture was stirred at 0° C. for 1 hr and at 20° C. for 1 hr at which point 10 mL of isopropyl alcohol was added and the solvent was removed in vacuo.

The residue was applied to a 330 g silica (gold) column in a minimum volume of chloroform and the column was eluted with 0-5% isopropyl alcohol in methylene chloride at 200 mL/min. The fraction which eluted at 13-14 minutes as a single peak was isolated as 1.3 g of yellow oil. AIBN initiated reaction of 50 mg of this material displayed a hard pellet.

Example 7

Dithio Ester

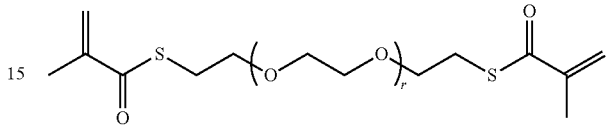

To 40 mL of dry tetrahydrofuran (THF), at 0° C., containing 0.4 mL (4 mmol) of methacryloyl chloride was added 20 mL of dry THF containing 2.0 g (1.33 mmol) of poly (ethylene glycol) dithiol 1500 mw and 0.7 mL (4.0 mmol) diisopropylethylamine, dropwise over 5 min, with rapid stirring. After stirring for 2 hrs, the reaction mixture was warmed to room temperature and solvent was removed in vacuo. Then, 100 mL of chloroform was used to dissolve reaction mixture and this was removed in vacuo, to entrain methacryloyl chloride.

The reaction mixture was placed on the vacuum line overnight at approximately 30 microns and a yellow solid formed. AIBN initiated reaction of 50 mg of this in 50 microliters of isopropyl alcohol resulted in a sponge of yellow gel.

Example 8

Jeffamine Glycidyl Amine

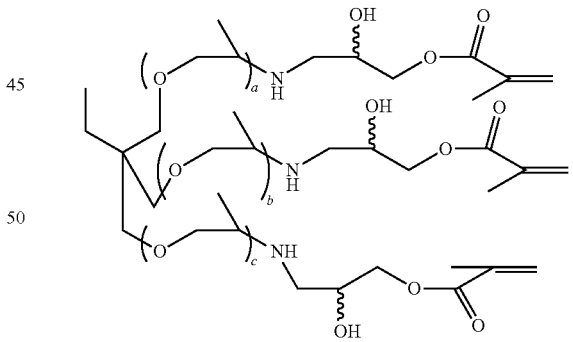

To 11 g of Jeffamine (25 mmol) is added 10.5 g of glycidyl methacrylate (75 mmol) followed by 4 g of silica gel and 100 mg of butylated hydroxytoluene. The reaction mixture was stirred at 20° C. After 2 hrs, 50 mL of chloroform was added to the thickening reaction mixture and stirring was continued. After another 18 hrs, an additional 200 mL of chloroform was added and the reaction mixture was filtered to remove silica gel and most of the solvent removed in vacuo. The residue was dissolved in 20 mL of isopropyl alcohol to give 40 mL of approximately 50% of Jeffamine glycidyl amine.

Example 9

Particle Prepared with a Glycidyl-Based Crosslinker

A prepolymer solution was prepared by dissolving 6.2 g of acrylamide, 14.6 g of 3-sulfopropyl acrylate potassium salt, and 0.3 g of a glycidyl-based crosslinker, prepared as in Example 1, in 20.0 g of distilled water. This solution was filtered and then vacuum degassed for 5 min and flushed with argon. A liter of mineral oil was sonicated for 1 hr and then added to a sealed reaction vessel equipped with an overhead stirring element. The vessel was vacuum degassed for at least 1 hr and then the vacuum replaced with argon. N,N,N',N'-tetramethylethylenediamine, approximately 3 mL, was added to the reaction vessel and overhead stirring started at 300 rpm. An initiator solution was made by dissolving 1.0 g of ammonium persulfate in 2.0 g of distilled water. The solution was filtered and approximately 550 µL were added to the prepolymer solution. After mixing, the solution was added to the reaction vessel. After 5 to 10 min, a solution of 0.35 mL of SPAN®80 in 10 mL of mineral oil was added and the resulting suspension was allowed to polymerize for at least 4 hr.

Example 10

Particle Prepared with a Peptide Crosslinker

A prepolymer solution was prepared by dissolving 3.8 g of acrylamide, 5.4 g of 3-sulfopropyl acrylate potassium salt, and 0.05 g of a peptide-based crosslinker, prepared as in Example 2, in 10.0 g of distilled water. This solution was filtered and then vacuum degassed for 5 min and flushed with argon. Mineral oil (300 mL) was sonicated for 1 hr and then added to a sealed reaction vessel equipped with an overhead stirring element. The vessel was vacuum degassed for 1 hr and then the vacuum replaced with argon. N,N,N',N'-tetramethylethylenediamine (2 mL) was added to the reaction vessel and overhead stirring started at 300 rpm. An initiator solution was made by dissolving 1.0 g of ammonium persulfate in 2.0 g of distilled water. The solution was filtered and 300 µL were added to the prepolymer solution. After mixing, the solution was added to the reaction vessel. After 5 to 10 min, a solution of 0.5 mL of SPAN®80 in 10 mL of mineral oil was added and the resulting suspension was allowed to polymerize for 5 hr.

Example 11

Purification of Particles

After the polymerization was complete, the mineral oil was decanted from the reaction vessel and the polymer particles were washed four times with fresh portions of hexane to remove the mineral oil. The particles were then transferred to a separatory funnel with phosphate buffered saline (PBS) and separated from residual mineral oil and hexane. The resulting mixture was washed twice with PBS.

The particles were separated into sizes using sieving. Sieves were stacked from the largest size (on top) to the smallest size (on bottom). A sieve shaker was utilized to aid the sieving process. The particles were placed on the top sieve along with PBS. Once all the particles had been sorted, they were collected and placed in bottles according to their sizes.

After sieving, the particles were dehydrated to extend their shelf life. Under stirring, the particles were placed in a graded series of solvent/water mixtures. Both acetone and ethanol were used successfully to dehydrate the particles. For at least 4 hrs, the particles were suspended in 75% solvent, 85% solvent, 95% solvent, 97% solvent, and 100% solvent. Subsequently, the particles were lyophilized, packaged, and sterilized.

Example 12

Determination of Delivery Characteristics of the Particles

To evaluate the delivery characteristics, particles prepared in a similar manner to Example 9 were injected through a Headway 17 microcatheter (0.017", 432 µm inner lumen) with a figure-eight knot of 4.5×1.5 cm. The test sample was prepared by mixing 2 to 3 mL of particles, 3 to 4 mL of saline, and 4 to 5 mL of contrast. The samples were injected through the microcatheter and into a dish using a 1 mL syringe. Pictures were taken of the particles before and after injection through the microcatheter. The diameter and the circularity of the particles was determined using Axiovision image analysis software. The table below summarizes the results.

In some embodiments, the form factor of a region describes the form of a region on the basis of its circularity. A perfect circle is given the value 1. The more elongated the region is, the smaller the form factor. The calculation is based on the Area filled and Perimeter Crofton parameters.

|  |  | Pre-Injection | Post-injection |
|---|---|---|---|
| 0.25% Crosslinker | Circularity | 0.94 ± 0.05 | 0.97 ± 0.02 |
|  | Diameter | 0.38 ± 0.09 mm | 0.48 ± 0.11 mm |
| 0.5% Crosslinker | Circularity | 0.99 ± 0.01 | 0.96 ± 0.08 |
|  | Diameter | 0.43 ± 0.13 mm | 0.47 ± 0.09 mm |
| 0.75% Crosslinker | Circularity | 0.93 ± 0.11 | 0.98 ± 0.01 |
|  | Diameter | 0.49 ± 0.10 mm | 0.45 ± 0.08 mm |

No change in the circularity or diameter of the particles was observed, indicating that the particles did not break apart or fragment during delivery through a micro catheter. In other words, the particles remained substantially intact when delivered through a catheter.

Example 13

Determination of In Vitro Hydrolytic Degradability

Samples of particles prepared with differing amounts of crosslinker were placed in PBS and stored at 37° C. to determine degradation time. The visual analysis included color and transparency of the particles, ability to see the particle outline, and the number of particles visible. The grading scale for the samples included (5) no change in particle numbers, outlines, or quantity from the beginning of the experiment, (3) faint particle outline with a good number of particles still visible, (1) very few particles visible, and (0) no particles observed in sample. Results are illustrated in FIG. 1. The results illustrate that degradation can be dependent on the crosslinker concentration. For example, the longest degradation time occurred with the largest crosslinker concentration.

Figure 2:
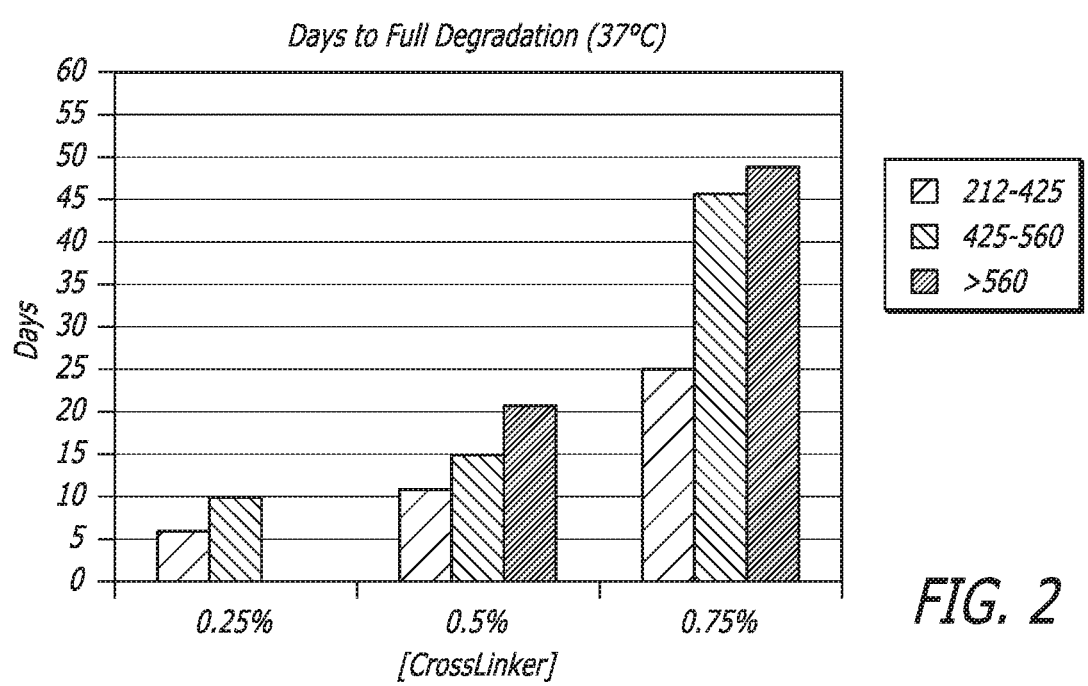
FIG. 2 is a graph showing time to full degradation for different polymer particles.

FIG. 2 graphically illustrates degradation time at 37° C. as a function of the amount of crosslinker. As illustrated, the greater the percentage of crosslinker, the longer degradation takes. Additionally, the larger the particle diameter (numbers on right of graph in micrometers), the longer the degradation. As such, the particles with the longest degradation time are those that have the largest concentration of crosslinker and the largest diameter. These two properties can be varied to tailor degradation time as needed.

Example 14

Tetra Ester Crosslinker

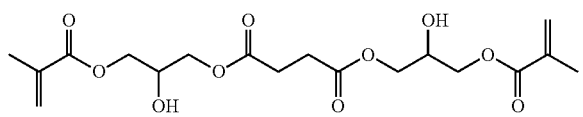 [SMILES: C=C(C)C(=O)OCC(O)COC(=O)CCC(=O)OCC(O)COC(=O)C(=C)C]

To a 200 mL pear-shaped flask, 10 g (84.8 mmol) of succinic acid, 40 g (0.689 mol) of allyl alcohol and 30 µL of 98% $H_2SO_4$ were added. The reaction mixture was refluxed for 6 hrs and then quenched by the addition of 25 mL of 1 M sodium carbonate solution. The solvent was removed under vacuum. The crude was reconstituted in 25 mL of water and the product, diallyl succinate, was extracted with ethyl acetate, 4×50 mL. The organic phase was collected and dried with $MgSO_4$ and the solvent was then removed in vacuo to give 9.26 g of diallyl succinate.

To a 1 L round bottom flask, 5.2 g (26.3 mmol) of diallyl succinate and 20 g (0.116 mol) of meta-chloroperoxybenzoic acid (mCPBA) were dissolved in 400 mL of dichloromethane. The reaction mixture was refluxed at 40° C. overnight. The reaction mixture was then passed through an Amberlyst free base column to remove the by-product, m-chlorobenzoic acid. The solvent was removed under vacuum to give the crude. Chromatography using ethyl acetate in hexane from 5% to 20% at 210 nm gave the pure diglycidyl succinate.

To a 20 mL vial, 1.15 g (5 mmol) of diglycidyl succinate, 950 mg (11 mmol) of methacrylic acid and 1.5 g (7 mmol) of 1-butyl-3-methylimidazolium bromide ([bmim]Br) were added. The reaction mixture was stirred at 75° C. After 1 hr, the TLC showed no presence of the epoxide. The reaction mixture was suspended in 50 mL of 1 M sodium carbonate solution and the product was extracted with ethyl acetate, 3×50 mL. The organic layer was collected and dried over $MgSO_4$, and then concentrated under vacuum. The TLC ran with 50:50 ethyl acetate:dichloromethane showed only one spot. Two grams of the title tetra ester crosslinker was collected with 99% yield.

Example 15

Tetra Thioester Crosslinker

To a 500 mL 3-neck round bottom flask under argon chilled at 0° C., 100 mL of dry THF was added. Under stirring, 20 g (0.11 mol) of 2,2'-(ethylenedioxy)ethanthiol and 16 mL (0.09 mol) of diisopropylethylamine were added. To 40 mL of dry THF, 5 mL (0.045 mol) of succinyl chloride was dissolved. Under argon, the solution was added drop wise into the reaction mixture at 0° C. via an addition funnel with vigorous stirring. Following the addition, the reaction mixture was stirred for 1 hr at 0° C. and then allowed to warm up to room temperature to stir overnight. The reaction mixture was then chilled on ice to precipitate the amine salt. The white precipitate was removed by filtering through a medium fritted glass filter and washed with ice cold THF. The filtrate was collected and concentrated under vacuum. Flash chromatography with ethyl acetate in DCM from 0% to 15% at 254 nm gave the dithiol ester intermediate.

To a 250 mL 3-neck round bottom flask under argon chilled at 0° C., 50 mL of dry THF was added. Under stirring, 3.17 g (7.1 mmol) of dithiol ester intermediate and 3.6 mL (20 mmol) of diisopropylethylamine were added. To 50 mL of dry THF, 2 mL (20 mmol) of methacryloyl chloride was dissolved. Under argon, the solution was added drop wise into the reaction mixture at 0° C. via an addition funnel with vigorous stirring. Following the addition, the reaction mixture was stirred for 1 hr at 0° C. and then allowed to warm up to room temperature to stir overnight. The reaction mixture was then chilled on ice to precipitate the amine salt. The white precipitate was removed by filtering through a medium fritted glass filter and washed with ice cold THF. The filtrate was collected and concentrated under vacuum. Flash chromatography with ethyl acetate in dichloromethane from 0% to 10% at 254 nm eluted the desired tetra thiol ester crosslinker from 4 min to 12 min. The mass spectrometry analysis gave 605.1 corresponding to [M+Na]$^+$ of the calculated mass of $C_{24}H_{38}O_8S_4$.

Example 16

Particle Prepared with a Peptide Crosslinker

A prepolymer solution was prepared by dissolving 3.1 g of acrylamide, 7.3 g of 3-sulfopropyl acrylate potassium salt, and 0.2 g of a peptide-based crosslinker, prepared as in Example 3, in 10.0 g of distilled water. This solution was filtered and then vacuum degassed for 5 min and flushed with argon. Mineral oil (500 mL) was sonicated for 1 hr and then added to a sealed reaction vessel equipped with an overhead stirring element. The vessel was vacuum degassed for at least 1 hr and then the vacuum replaced with argon. N,N,N',N'-tetramethylethylenediamine, approximately 2 mL, was added to the reaction vessel and overhead stirring started at 300 rpm. An initiator solution was made by dissolving 1.0 g of ammonium persulfate in 2.0 g of distilled water. The solution was filtered and approximately 250 µL added to the prepolymer solution. After mixing, the solution was added to the reaction vessel. Subsequently, a solution of

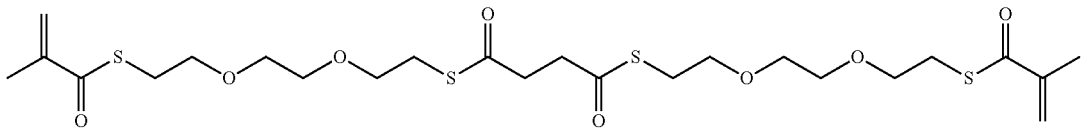 [SMILES: C=C(C)C(=O)SCCOCCOCCSC(=O)CCC(=O)SCCOCCOCCSC(=O)C(=C)C]

0.35 mL of SPAN®80 in 10 mL of mineral oil was added and the resulting suspension was allowed to polymerize for at least 4 hr.

Example 17

Determination of In Vitro Enzymatic Degradability

Samples of particles prepared with a peptide crosslinker were placed in PBS, with and without an enzyme, and incubated at 37° C. or 55° C. to determine degradation time. Samples included a high enzyme concentration and a low enzyme concentration.

Figure 3:
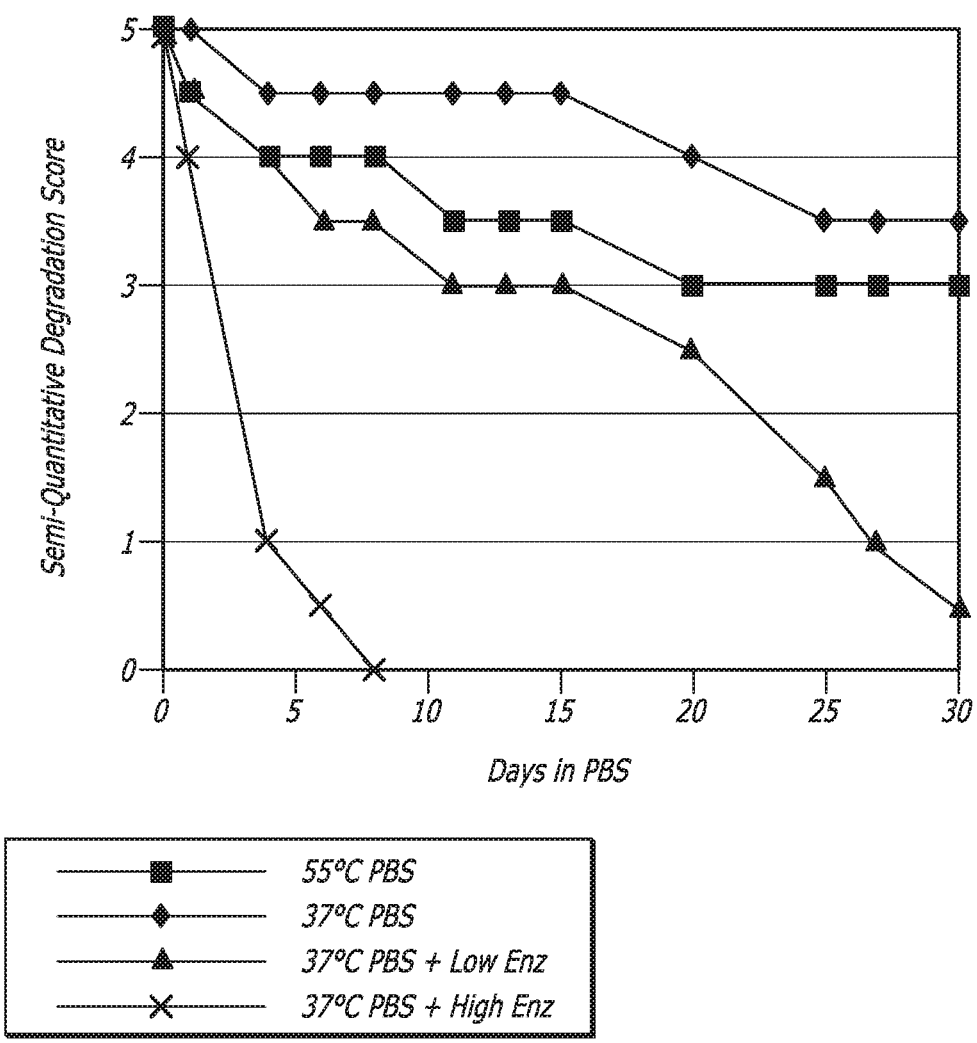
FIG. 3 is another graph showing scoring for polymer particle degradation.

The visual analysis included color and transparency of the particles, ability to see the particle outline, and the number of particles visible. The grading scale for the samples included (5) no change in particle numbers, outlines, or quantity from the beginning of the experiment, (3) faint particle outline with a good number of particles still visible, (1) very few particles visible, and (0) no particles observed in sample. Results are illustrated in FIG. 3. The results illustrate that the particles are slow to hydrolytically degrade, but the rate of degradation can be increased in the presence of an adequate enzyme. For example, the shortest degradation time occurred with the highest concentration of enzyme present in the PBS solution.

The preceding disclosures are illustrative embodiments. It should be appreciated by those of skill in the art that the devices, techniques and methods disclosed herein elucidate representative embodiments that function well in the practice of the present disclosure. However, those of skill in the art should, in light of the present disclosure, appreciate that many changes can be made in the specific embodiments that are disclosed and still obtain a like or similar result without departing from the spirit and scope of the invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects those of ordinary skill in the art to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Further, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:
1. An embolic solution including:
   1) polymer particles formed from a solution including at least one negatively charged monomer including at least one functional group, and at least one crosslinker; and at least one positively charged drug; or

2) polymer particles formed from a solution including at least one positively charged monomer including at least one functional group, and at least one crosslinker; and at least one negatively charged drug;
wherein the polymer particles have a spherical diameter between about 40 μm and about 1,200 μm.

2. The embolic solution of claim 1, wherein the polymer particles are susceptible to degradation through hydrolysis or enzymatic action, and wherein the degradation provides less than about 10% of the polymer particles intact after about 5 days.

3. The embolic solution of claim 1, wherein the spherical diameter is between about 75 μm and about 1,200 μm.

4. The embolic solution of claim 1, wherein the crosslinker includes at least two functional groups.

5. The embolic solution of claim 1, wherein the crosslinker includes at least one linkage susceptible to degradation through hydrolysis or enzymatic action.

6. The embolic solution of claim 1, wherein the at least one crosslinker is bis-glycidyl amino alcohol,

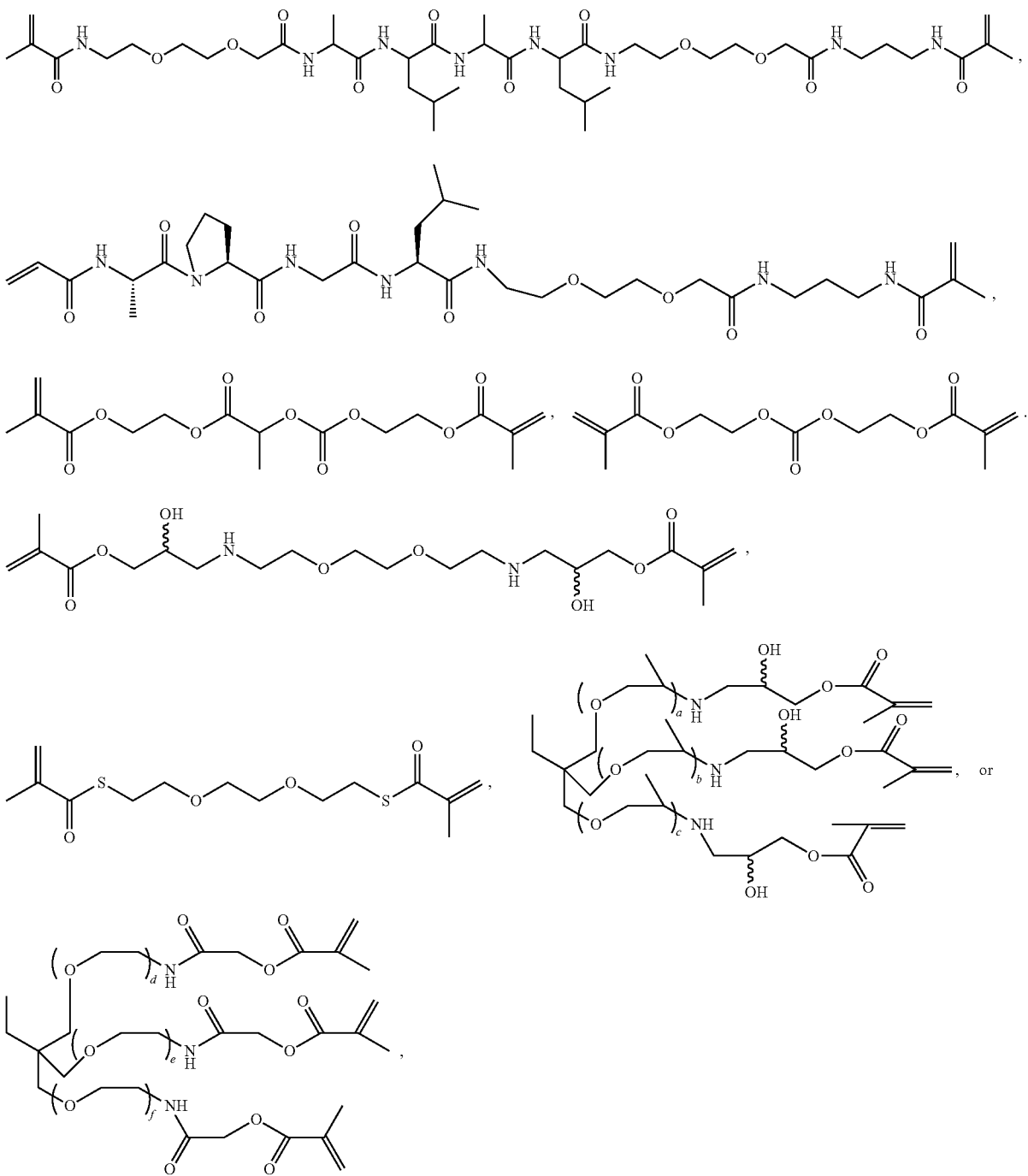

wherein a, b, c, d, e, and f are each independently 1-20.

7. The embolic solution of claim 5, wherein the at least one linkage is an ester, a thioester, a carbonate, a peptide cleavable by matrix metalloproteinases, a peptide cleavable by matrix collagenases, a peptide cleavable by matrix elastases, a peptide cleavable by matrix cathepsins, or a combination thereof.

8. The embolic solution of claim 1, wherein the crosslinker is bis-glycidyl amino alcohol or bi-functionalized methacryloyl-Ala-Pro-Gly-Leu-AEE-methacrylate.

9. The embolic solution of claim 1, including:
polymer particles formed from a solution including at least one negatively charged monomer including at least one functional group, and at least one crosslinker; and
at least one positively charged drug.

10. The embolic solution of claim 9, wherein the at least one negatively charged monomer includes an acidic moiety.

11. The embolic solution of claim 9, wherein the at least one negatively charged monomer includes a carboxylic acid.

12. The embolic solution of claim 10, wherein the at least one negatively charged monomer is acrylic acid, methacrylic acid, 3-sulfopropyl acrylate, 3-sulfopropyl methacrylate, a derivative thereof, a combination thereof, or a salt thereof.

13. The embolic solution of claim 1, including:
polymer particles formed from a solution including at least one positively charged monomer including at least one functional group, and at least one crosslinker; and
at least one negatively charged drug.

14. The embolic solution of claim 13, wherein the at least one positively charged monomer includes a basic moiety.

15. The embolic solution of claim 14, wherein the at least one positively charged monomer includes an amine.

16. The embolic solution of claim 14, wherein the at least one positively charged monomer is amino ethyl methacrylate, aminopropyl methacrylate, a derivative thereof, a combination thereof, or a salt thereof.

17. The embolic solution of claim 1, wherein the composition is sterilized.

18. The embolic solution of claim 1 including a radiopaque contrast agent.

19. The embolic solution of claim 1 including a dye.

20. The embolic solution of claim 1, wherein the polymer particles have a circularity greater than about 0.9.

* * * * *